United States Patent [19]

Squire

[11] Patent Number: 4,760,782
[45] Date of Patent: Aug. 2, 1988

[54] DENTAL AMALGAM PRESS

[76] Inventor: Molly A. Squire, P.O. Box 2312, Malibu, Calif. 90265

[21] Appl. No.: 31,859

[22] Filed: Mar. 30, 1987

[51] Int. Cl.$^4$ .............................................. B30B 9/06
[52] U.S. Cl. .................................. 100/116; 100/132; 100/282
[58] Field of Search ............... 100/282, 116, 126, 132, 100/110, 213; 210/399; 209/48

[56] References Cited

U.S. PATENT DOCUMENTS

| | | | |
|---|---|---|---|
| 1,934,042 | 11/1933 | Craigo | 100/116 |
| 2,399,834 | 5/1946 | Seltzer | 100/213 X |
| 3,052,985 | 9/1962 | Harvey | 100/116 X |
| 4,079,516 | 3/1978 | Marshall | 100/110 X |

Primary Examiner—Andrew M. Falik
Attorney, Agent, or Firm—Roger A. Marrs

[57] ABSTRACT

A press for use by either right or left-handed persons, having a press cavity defined between a stationary base and a movable curvilinear wall member for manually receiving a bagged amount of mercury and amalgam mixture. A resilient yieldable turning element is operably connected to the base and a movable wall for progressively advancing the wall member towards the base to pressably engage the bagged mixture so that the mixture is forced through fibers or cloth of the bag in a condition ready for dental use. A globe encases the press to contain released vapors and a well is disposed beneath the press to collect excess mercury or amalgam during the pressing procedure.

7 Claims, 2 Drawing Sheets

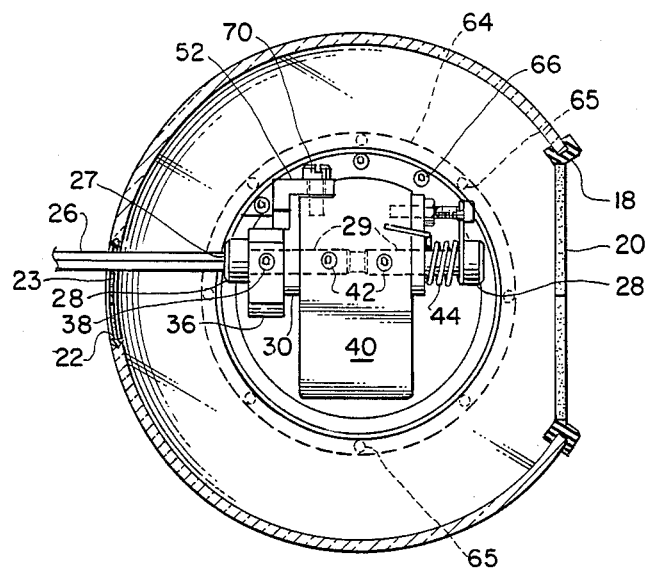
FIG. 3.
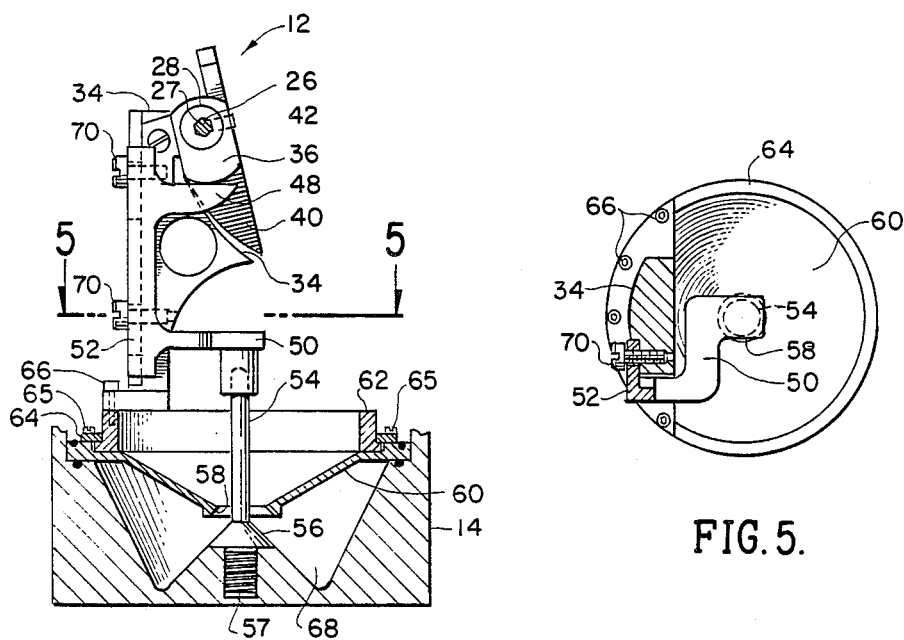
FIG. 4.
FIG. 5.

4,760,782

DENTAL AMALGAM PRESS

BACKGROUND OF THE INVENTION

1. Field of the Invention

The present invention relates pressing devices and more particularly to a novel press for use in the preparation of dental amalgam fillings utilizing a quantity of mercury so that the processing is safe and non-contaminating to personnel.

2. Brief Description of the Prior Art

In the dental industry, it is common to use mercury in the formation of amalgam fillings, referred to as "silver fillings". Over two pounds of mercury are used every year in the average dental office for such preparation. In the preparation, mercury vapor levels often become elevated due to poor storage, leaking containers, open mixers, accidental spillage and poor ventilation. Chronic occupational exposure by dental personnel to such released mercury vapors often leads to mercury poisoning, sickness and poor performance.

In some instances, attempts have been made to control released mercury vapors by employing fans and vacuum systems so that the air is filtered around the mercury usage areas. The storage and handling of mercury is still unsatisfactory in such a filtering environment, in that it is frequently handled in a piece of cloth between the finger and thumb of the dental assistants when preparing the amalgam mixture preparatory for condensing into the amalgam carrier and tooth of the dental patient. In most instances, the silver amalgam and mercury are obtained in premeasured capsules for mixing. The size of the filling and the number of fillings to be done at one time determine the quantity of mercury necessary in a given mixture. This oftentimes necessitates handling the amalgam mixture to express extra mercury from the mixture for the fillings.

Therefore, a widespread need has existed in the dental industry to provide a means for handling the amalgam mixture while expressing the excess mercury from the dental amalgam. Preferably, the means should take the form of a tool such as a press which would store mercury immediately upon expression from the amalgam, and also prevent release of the mercury into the surrounding environment through vapor released into the air or by physical contact in handling the amalgam mixture.

SUMMARY OF THE INVENTION

Accordingly, the above problems and difficulties are obviated by the present invention which provides a novel press apparatus for extracting or expressing mercury from amalgam, that provides an enclosure which houses a cam-type press so that released mercury vapors are contained within the housing, and which further includes a well for receiving quantities of mercury spilled during the pressing procedure. The press includes a base carried on a frame which mounts an arcuate cam having a pressing surface defining a cavity in combination with the base for receiving a quantity of amalgam mixture intended to be pressed. The amalgam is introduced into the cavity in a cloth bag by fingers of the user, and means for rotating the cam into contact with the bag are operably carried on the frame. Access ports are provided in the housing enclosing the press for insertion of the user's hand as well as for permitting the handle of the moving means to be exposed exteriorly for grasping by the hand of the user. A feature resides in providing slot means in the housing for rotating the housing on the base whereby the port is placed or oriented with respect to the base to permit left or right-handed persons to operate the press. Also, means are provided for collecting excess mercury or residue from the pressing operation.

Therefore, it is among the primary objects of the present invention to provide a novel means for controlling the vapors and contact with a mercury product so that the handling thereof by attendant personnel is safe and protective.

Still another object of the present invention is to provide a novel pressing means for expressing mercury from an amalgam mixture wherein released vapors are controlled and excess quantities of waste mercury are stored harmlessly.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 3 is a transverse cross-sectional view of the press apparatus shown in FIG. 1 as taken in the direction of arrows 3—3 thereof;

FIG. 4 is a fragmentary sectional view of the press and well used in the press apparatus of FIGS. 1-3 inclusive; and FIG. 5 is a cross-sectional view of the press shown in FIG. 4 taken in the direction of arrows 5—5 thereof.

DESCRIPTION OF THE PREFERRED EMBODIMENT

Figure 1:
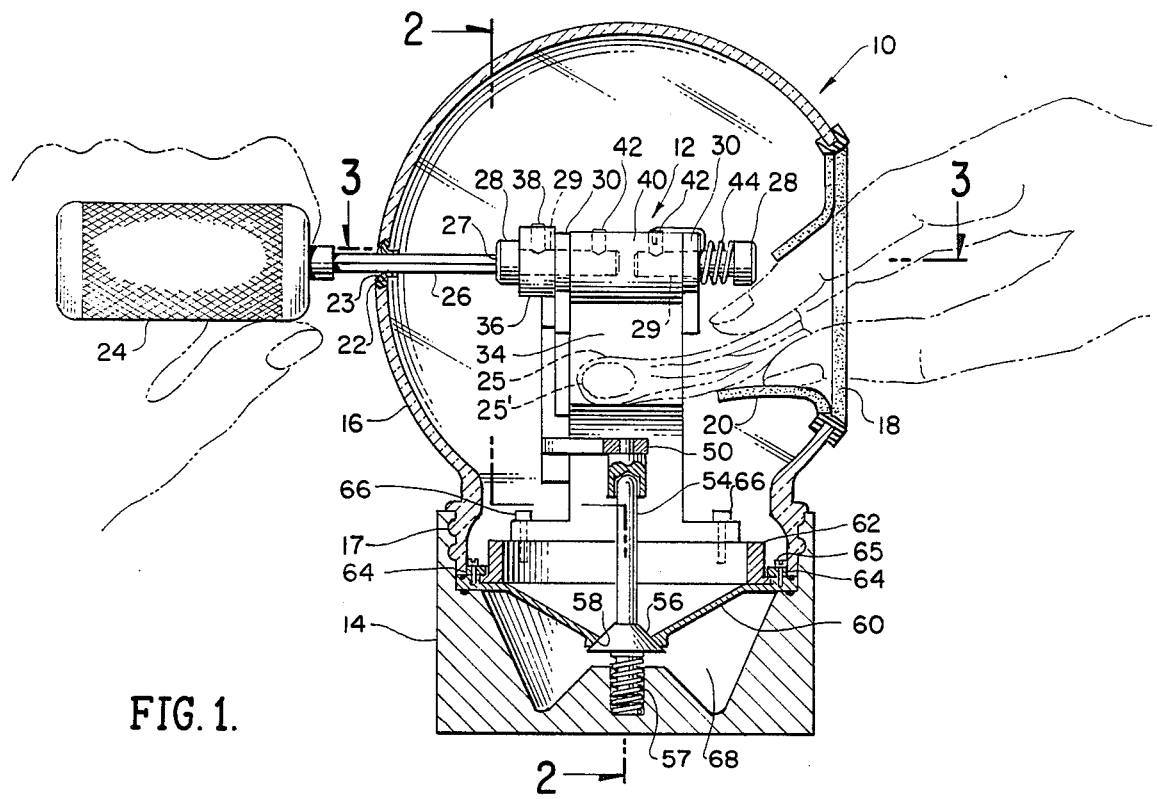
FIG. 1 is a longitudinal cross-sectional view of the novel press of the present invention.

Referring to FIG. 1, the dental amalgam press 10 comprises press mechanism 12 and mercury retriever base 14 encased in a glass globe 16 defining a press cavity and attached by screwing to the base 14 by means of threads 17 and having a covered semi-sealed port or opening 18 with slitted flexible rubber-like cover 20. A round opening 22 on the opposite side of the globe 16 with a flexible closure seal 23 is provided wherein a handle 24 can be inserted. The handle 24 has a knurled surface to aid the user in gripping. To operate the press mechanism 12, a long hexagonal shaft 26 extending from the handle 24 is inserted into a hexagonal recess 27 of the head 28 of the cap screw 29. Two cap screws 29 opposing each other function as a rotatable shaft in bearing blocks 30 attached by screws 42 on both sides of main base 34. On one screw 29 a rotatable cam 36 is attached to screw 29 by means of set screw 38 and the pressure cam arm 40 is attached to both screws 29 by means of set screws 42. A torque spring 44 returns cam arm 40 to its original retracted horizontal position as shown in FIGS. 1 and 2.

Figure 2:
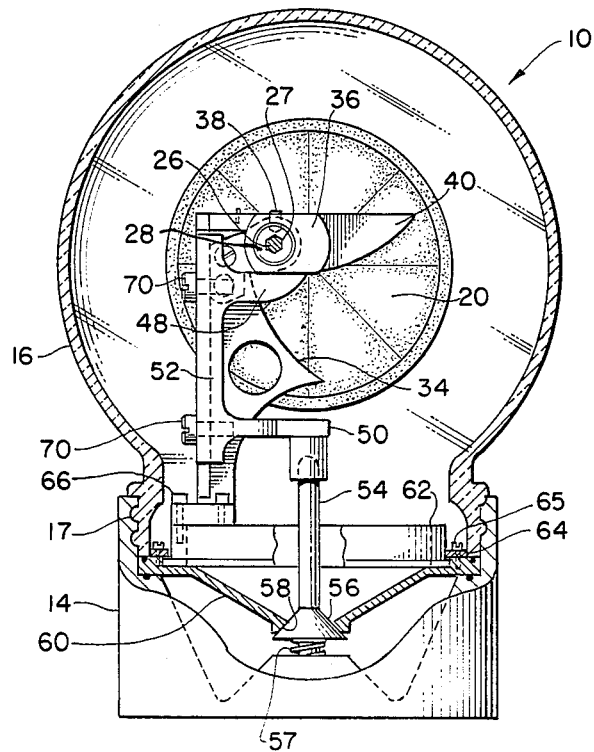
FIG. 2 is a longitudinal cross-sectional view of the press shown in FIG. 1 as taken in the direction of arrows 2—2 thereof.

As illustrated in FIG. 1, the left hand of the user is turning the handle 24 clockwise as viewed in FIG. 2 to activate the press unit 12. The right hand is holding amalgam squeeze cloth 25 passed in through the opening 18. The amalgam 25 in the squeeze cloth 25 is resting in the bottom dish 34 of the cam press 12. The excess mercury is expressed through the cloth and rolls down through the opening 58 into the base 14 where this excess mercury is stored.

Referring now to FIG. 2, when the cam arm 40 is rotated in a clockwise direction, the camming surface integrally attached with the cam arm 40, forces the slidable activating cam arm 48 in downward direction. A secondary arm 50 extending from the slide 52 pushes plunger 54 in downward direction thus releasing conical stopper 56 from drain hole opening 58 and depressed compression spring 57. Thus the stopper 56 retracts from the opening 58 in the funnel 60 located in the base 14. This action of cam 36 against cam arm 48 is best shown in FIG. 4.

FIG. 2 illustrates the press mechanism 12 in an inoperative position. In rest position, the cam arm 40 is held in a fully open position. The base 14 has a funnel shaped storage area 68 for holding a reservior of glycerine or oil-based solution to capture mercury vapors. The internal cavity of the base 14 for storage of the vapors is highest farthest from the center opening 58. This helps to trap any vapor farthest from the opening 58. The conical plunger 56 is designed to deflect entering mercury away from the opening 58.

Referring to FIG. 3, from the top, the press mechanism 12 is seen through the glass dome 16 as in FIG. 4. The hexagonal shaft 26 is seen going through the seal in opening 22. The shaft enters the hexagonal recess 27 of head of cap screw 28. The cap screw 29 enters the press unit 12 under the pressure cam arm 40 which is seen at rest position. The base platform swivel ring 62 is mounted upon the total press mechanism 12 and fastened by screws 66.

The unit is at rest with the cam arm 40 fully open. The flexible rubber-like cover 20 is at rest position, fully sealing the opening 18.

Referring now to FIGS. 3 and 4, the base 34 of press mechanism 12 is mounted on a rotatable base ring 62. The base ring 62 is held in place under a retaining ring 64 which is anchored to the base 14 by screws 65. The entire press mechanism 12 is thus able to rotate 180° or a full 360° to enable right or left-handed manipulation of the handle 24 while maintaining a view of the amalgam mix in the press. The mercury expressed by the press 12 is channelled by the funnel surface slope of 60 and passes through the opening 58. It is shed outward in the chamber, away from directly under the opening by the slope of the stopper 56. The expressed mercury lands in the holding as well area 68 of the base 14. The holding area is shaped to direct any fumes away from the center opening 58 and trap them within the internal cavity in the base 14. The chamber is also filled with glycerine or a heavy oil-based liquid to impede evaporation into the atmosphere of the chamber.

The partial sectional view in FIG. 4 shows the plunger 56 depressed, clearing the opening 58, thus allowing the extruded mercury to run down into the base 14 for storage. The press mechanism 12 is shown in mid-action, with the cam arm 40 rotated in a clockwise direction by the hexagonal shaft 26 inserted in the head 28 of the screw 29 thus pressing the amalgam mix against the cam base 34. Concurrent with the above action the slide arm 52 is pushed downward by the cam 36, which in turn depresses the stopper 56 by means of the arm 50. The configuration of the arm 50 is best shown in FIG. 5.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A dental amalgam press for expressing mercury from an amalgam mixture, comprising:
   a transparent housing;
   a press operably carried inside said housing having a stationary base and a movable press member defining a press cavity therebetween for receiving said amalgam;
   movable means for actuating said movable press member towards and away from said stationary member to close said cavity and pressably engage with said amalgam to express mercury therefrom;
   said movable means including a handle external of said housing from one side thereof for manual manipulation by the user and connectable to said movable member within said housing; and
   said housing having a semi-sealed port located on its side opposite to its side associated with said movable means allowing insertable introduction of said amalgam into said press cavity by said user.

2. The invention as defined in claim 1 including:
   a well provided in said stationary member in alignment with said press cavity for receiving excessive expressed mercury from said amalgam via gravitional force.

3. The invention as defined in claim 2 wherein:
   said press includes a curvilinear surface provided on said stationary member and a conformal curved surface on said movable member adapted to progressively mate during the pressing procedure.

4. The invention as defined in claim 3 wherein:
   said housing includes a plurality of flexible overlapping segments radially arranged across said housing port yieldable to permit passage of the user's fingers therethrough.

5. The invention as defined in claim 4 wherein:
   said movable member is rotatably carried on said stationary member;
   resilient means normally biasing said movable member curved surface away from and out of conformal engagement with said mating curved surface of said stationary member.

6. The invention as defined in claim 5 wherein:
   said stationary member well terminates in an opening leading to a reservoir for collecting mercury;
   a plunger movable with respect to said stationary member in response to said movable member;
   said plunger having a stopper carried on one end for selectively opening and closing said opening in accordance with the pressing and cessation of pressing within said press cavity respectively.

7. The invention as defined in claim 6 wherein:
   said housing is a globe and said stationary member includes a base supporting said well;
   said globe rotatable on said base between a pair of positions associated with operation of said press by either right or left-handed persons.

* * * * *